United States Patent [19]

Urist

[11] Patent Number: 4,526,909
[45] Date of Patent: Jul. 2, 1985

[54] POLYMETHYLMETHACRYLATE DELIVERY SYSTEM FOR BONE MORPHOGENETIC PROTEIN

[75] Inventor: Marshall R. Urist, Pacific Palisades, Calif.

[73] Assignee: Regents of the University of California, Berkeley, Calif.

[21] Appl. No.: 569,031

[22] Filed: Jan. 9, 1984

[51] Int. Cl.³ .................. A61K 35/12; A61K 37/00; A01N 63/02
[52] U.S. Cl. .................................. 523/115; 424/95; 524/17; 514/21
[58] Field of Search .................. 523/115; 524/17; 424/95, 177

[56] References Cited

U.S. PATENT DOCUMENTS 4,294,753 10/1981 Urist ................................ 424/95

Primary Examiner—Harold D. Anderson
Attorney, Agent, or Firm—Kenyon & Kenyon

[57] ABSTRACT

A delivery system for delivering bone morphogenetic protein to induce formation of new bone in viable tissue. The delivery composition comprises substantially pure bone morphogenetic protein and polymethylmethacrylate and it is prepared by admixing the bone morphogenetic protein and polymethylmethacrylate. The composition is implanted in viable tissue where the bone morphogenetic protein is slowly released and induces formation of new bone.

10 Claims, No Drawings

POLYMETHYLMETHACRYLATE DELIVERY SYSTEM FOR BONE MORPHOGENETIC PROTEIN

This invention was made with Government support under Grant No. DE 02103 awarded by the Department of Health and Human Services. The Government has certain rights in this invention.

This invention relates to compositions and methods for delivering bone morphogenetic protein (BMP) to viable bone and other skeletal tissues. More specifically, the invention relates to such delivery systems for BMP utilized in bone implants, and comprises compositions that are admixtures of polymethylmethacrylate (PMMA) and BMP. The delivery composition may thus be applied to defective bone tissue to induce formation of new bone. The invention also relates to the preparation of such bone implant compositions and the method of using such compositions as bone implants.

BMP is a relatively low molecular weight protein or protein implant that is isolated from dentin, bone and other skeletal tissues by chemical extraction and differentiation percipitation. BMP induces perivascular mesenchymal type cells to differentiate into cartilage and bone endochrondal ossification. BMP may be isolated in relatively pure form by processes described in U.S. Pat. No. 4,294,753 and in copending patent applications Ser. No. 260,726 filed May 5, 1981, now U.S. Pat. No. 4,455,256. BMP, and processes for its isolation and more complete purification are further described in Ser. No. 523,606 filed Aug. 16, 1983. The disclosures in said patent and applications are incorporated herein by reference.

Said patent and patent applications disclose that BMP may be implanted directly into a bone defect where it stimulates differentiation of connective tissue into bone and thereby repairs the defect. After about six months remodeling is substantially complete, and about 1 gram of bone is produced for each milligram of BMP implanted. Such levels of bone induction have been observed when a relatively high proportion of BMP is initially used in the implant. Otherwise, at lower total BMP levels new bone induction is substantially reduced or no induction at all takes place. For example, when up to 1 mg. of BMP was inserted into a mouse muscle pouch, BMP was rapidly absorbed and did not induce formation of grossly visible deposits of new bone. Moreover, the nature (metabolic rate) of the animal subject under treatment is a major determinative as to the minimum quantity of BMP that will induce new bone formation.

The present invention provides a composition and method for greatly increasing the amount of new bone induced to be formed by a given amount of substantially pure BMP. Particularly, the threshold quantity of BMP required to induce new bone formation is substantially reduced. It has now been discovered that a delivery system for BMP comprising PMMA and BMP allows the BMP to be delivered on a sustained basis to the host bone with the expectation that bone formation will be induced for a period of years. The BMP-PMMA composition of this invention provides sustained delivery of BMP and causes stimulation of host bed new bone formation for a period believed to be eight years or more. Moreover, the quantity of bone that is induced for a given amount of BMP implanted in the BMP-PMMA delivery composition described herein has been found to be significantly higher when compared with new bone formation induced by BMP in the absence of PMMA. For example, as shown herein, 1 mg. of BMP in combination with 16 mg. of powder PMMA induced approximately 30 $mm^3$ of new bone in a mouse muscle pouch, whereas implants of 1 mg. quantities of BMP without PMMA did not produce any new bone. Thus, the present invention allows for substantially reduced quantities of BMP to be used in bone implants, and yet results in the induced formation of significant quantities of new bone. The observation that the BMP-PMMA composition of this invention induces formation of large quantities of new bone from smaller quantities of BMP compared to implants of BMP dispersed in the tissues without PMMA, suggests that slow absorption in a locally sustained concentration gradient of BMP enhances the bone morphogenetic response.

BMP delivered by the system of this invention induces differentiation of bone by the host bed connective tissues surrounding the implant into bone. Other advantages of the BMP-PMMA sustained delivery system include, (1) continuous proliferation of new bone for continuous reinforcement of the host bone bed, (2) ingrowth of bone into the PMMA surfaces and interior crevices, and (3) prevention of loosening of joint implants in young active patients.

The most commonly used luting cement for orthopedic and cranial reconstructive operations is polymethylmethacrylate. A luting cement fills the space between prosthetic implants and host beds. A description of the methods of the operation of luting cements is described in, Orthopedic Surgery: A Weekly Update, Vol. 1, No. 15, 1980, "Polymers in Orthopedic Surgery", Weinstein.

In accordance with the present invention other acrylic polymers such as those known in the art for preparation of artificial bone implants may also be used. However, PMMA is preferred because it is believed that PMMA provides more advantages than the other acrylics.

Briefly, the present invention comprises admixing PMMA and BMP to form the active delivery composition of the delivery system. Other additives may be included in the admixture, each for its own particular function. For example, there may also be included in the composition, radioopacifying agents, antibiotics, prosthesis devices, and the like. In preferred embodiments, the BMP-PMMA delivery composition is formed into a dough and shaped as desired. Usually, the dough is prepared by adding some liquid methylmethacrylate (MMA) monomer to the mixed PMMA-BMP powder, and then further mixing the ingredients. The monomer will start to polymerize during the mixing step and therefore the dough should be shaped as desired prior to complete polymerization of the monomer.

Commercial preparations (known as bone cements) are available. They contain PMMA and are specifically designed as bone implant materials to secure prosthesis devices. For example the product sold under the name Zimmer Bone Cement by Zimmer Inc. of Warsaw, Ind., has been used in connection with this invention. Also available is a PMMA-containing product sold under the name Surgical Simplex by Howmedica, Inc. See U.S. Pat. No. 4,341,691. Generally, bone cements are supplied as a PMMA powder component in the homopolymeric form, and a MMA liquid component in the monomeric form. The proportion of the components comprise a liquid component to powder component ratio of one to two (volume/weight) where the volume is in milliliters and the weight is measured in grams.

BMP is prepared in powder form as set forth in the above referred to patent and applications. Either purified BMP or its co-precipitate with tricalcium phosphate may be used. Shortly before use the BMP and PMMA powders are mixed together. Thereafter, it is preferable to add the liquid MMA monomer to form the doughy composition. While still in the doughy stage, namely before substantial polymerization of the MMA, the composition may be formed into small pellets and allowed to dry or harden. The composition may be supplemented with other agents as desired, such as radioopacifying agents (barium sulfate) and antibiotics (e.g., gentamyicin or silver sulfate). Such additives have been known and used in connection with PMMA bone cement materials. See, for example, J. Bone Joint Surg., 63A; 798, 1981, "The Depot Administration of Penicillin G and Gentamyicin in Acrylic Bone Cement", Hoff et al.; And, Clin. Orthop., 169:264–268, 1982, "Silver Antibacterial Cement. Comparison with gentamyicin in experimental osteomyeolitis", Dueland et al. The proportions of the additive are well known, for example between 6 and 12 percent by weight of the composition may be barium sulfate.

The composition is self curing and expands into the host bed prior to hardening. As in prior PMMA bone implant work, it is believed that the process of bone repair when the compositions of the present invention are implanted in a defective bone, involves formation of a fibrous membrane of variable thickness at the composition-bone interface. The thickness of the fibrous membrane is determined by the density and surface area of the host bed. In bone implant work the thickness of the membrane gradually increases with time and loosening of the implant. Acrylic cements, and particularly PMMA, are remarkably well tolerated in implant work and are even permeable to body fluids. Unless there is a microfracture or loosening due to host bed resorption, the acrylic cement is virtually inert.

The components of the BMP delivery composition of this invention may be varied as desired within a fairly broad range. As shown in Table I, the rate of increase in the volume of new bone induced by the BMP-PMMA delivery composition begins to fall off in the higher range of BMP in the delivery composition. Generally, induced new bone may be noted with as little as about 0.05–0.1 mg. BMP/16 mg. PMMA.* The upper range of BMP may be varied as required, bearing in mind that the efficiency of the formation of induced new bone falls off with increasing proportion of BMP. As a practical matter, the upper range in the ratio of between about 0.5–2 mg. BMP/16 mg. PMMA* in the delivery composition is preferred.

* The PMMA proportion is the weight of the dry PMMA powder component admixed with the BMP, and before addition of the liquid MMA monomer component. Depending upon evaporation rates, the MMA monomer may contribute up to about 8 mg. of additional PMMA to the delivery composition.

TABLE I

| Mg. BMP/16 Mg. PMMA* | Mm$^3$ New Bone (After 21 Days) |
|---|---|
| 0 | 0 |
| 0.1 | 1 |
| 0.2 | 4 |
| 0.5 | 20 |
| 1.0 | 30 |

In practice, the delivery composition is prepared in the desired ratio, and is implanted in the course of a surgical procedure. New bone formation is radiologically observed within about 10–60 days after implant, depending on the subject animal. Bone formation continues to be induced over an extended period believed to be upward of eight years.

BMP implant tests performed without PMMA indicate that formation of new bone requires a higher threshold quantity of BMP, and the rate of increase of new bone formation falls off very rapidly about 5 mg. of BMP in the implant. Table II shows the high threshold of BMP required to induce new bone formation, and the rapid fall off in the rate of new bone formation.

TABLE II

| Mg. BMP | Mm$^3$ New Bone (After 21 Days) |
|---|---|
| 0.5 | 0 |
| 1 | 0 |
| 2 | 0.5 |
| 5 | 40.0 |
| 10 | 44.0 |

The data in Tables I and II were based upon measurements of gross bone induction in implants in muscle pouches of mice of the quantities of BMP shown.

EXAMPLE 1

Bovine BMP (bBMP) was prepared from bovine bone matrix by the method described in Ser. No. 523,606. The relative pure BMP was mixed and blended with the powder PMMA component of Bone Cement obtained from Zimmer, Inc. Admixtures were prepared in a mortar pestle in the proportions shown in Table I. The composite powders of the PMMA component of the Bone Cement and bBMP were mixed with the liquid MMA monomer. The composition reached the doughy stage and before polymerization was complete the composite was cut into pellets measuring approximately 2 mm × 2 mm × 4 mm in volume, and each weighed about 16 mg. The pellets were allowed to dry overnight at room temperture. Prior to being used as implants, the pellets were gas sterilized in ethylene oxide.

The PMMA component of the Zimmer Bone Component is present in ratio of 2 parts by weight to 1 part by volume of the liquid MMA monomer components. Therefore, for example, for each 40 gms. of PMMA polymer used in the delivery system an additional 20 ml of MMA monomer is admixed with it. The liquid MMA monomer component contains, by volume, approximately 97.25% MMA monomer, 2.75% N,N-dimethyl-p-toluidine and about 80 ppm of hydroquinone. The PMMA polymer components contains about 89.25% PMMA, about 10% barium sulfate, and about 0.75% benzoyl peroxide. A maximum of 1% water may also be present in the polymer component.

It has been observed that barium sulfate in the BMP-PMMA delivery composition does not retard the diffusion of BMP out of the composition.

On the basis of the bone morphogenetic responses noted, the BMP-PMMA delivery composition induces formation of new bone by a sequence of morphological events that are observed in implants of BMP without PMMA. Moreover, observations of the pharmocokinetics of the release of organic substances, such as gentamyicin, from conventional PMMA bone cement systems, done in both in vitro and in vivo tests suggest that the mechanism is biphasic. In vitro tests have shown in initial phase (identified by the antibiotic half life) is terminal between 10 and 15 days. In the final phase, the half life is 30 days but detectable quantities are released for periods as long as five years. The most important observation is that 5 to 10 percent of the organic substance is readily initially released; and, the rate is determined by the surface area of the PMMA. Rates of release of the antibiotic for in vivo systems are not percisely calculable because of kidney reabsorption of the antibiotic. However, with due consideration for reabsorption, only 5 to 18 percent of the gentamyicin has been accounted for as released from PMMA over a 60 day period. It has been suggested that it has a terminal half life of at least 240 days. In general, observations on gentamyicin-PMMA delivery systems indicate that release of antibiotic from PMMA is a sustained and long term process. Thus, the known diffusion of antibiotic from PMMA, together with the observed induction of bone formation when the BMP-PMMA delivery composition of this invention is used as a bone implant evidences that BMP diffuses out of the PMMA and interacts biologically with the host bone tissue to induce a localized bone morphogenetic response.

The delivery compositions of this invention have relatively small masses and are used in relatively thin layers (i.e., in a range of 1 mm to 2 mm in thickness). The heats of solution and polymerization that are encountered in the process of preparing the delivery compositions are insufficient to denature the BMP. The relatively thin layer and small mass allows the heat to rapidly disipate, thereby avoiding an adverse affect on the BMP. Accordingly, the temperature of denaturization of BMP, in the range of 70° C. to 80° C., is not reached under the conditions hereof. However, in preparing larger batches of the delivery composition care must be taken to avoid heats of solution and polymerization that will adversely affect the BMP.

EXAMPLE 2

A delivery composition of BMP-PMMA was prepared as in Example 1. It contained 10 mg. of BMP in 100 mg. of PMMA, and about 11 mg. barium sulfate. It was implanted in the thigh of a mouse. After 21 days a roentgenogram was taken which showed densely radioopaque areas indicating the formation of new bone. The roentgenogram indicated that the bone and the residual PMMA were coextensive.

A similar implant experiment was performed using PMMA only, as a control. The PMMA induced formation of a relatively avascular fibrous connective tissue without any evidence of any bone formation anywhere in the thigh.

In terms of yield of new bone the implantation of a small dose of BMP-PMMA was equivalent to a large dose of BMP that was not incorporated in PMMA. This is particularly significant in view of the small amount of BMP that is initially released, i.e., as little as 5 to 10 percent of the total dose of BMP delivered by BMP-PMMA composition. The import of this discovery is of even greater significance in view of the sustained delivery of BMP over a period of months (and years are anticipated) after implantation thereby resulting in a steady local induction of bone formation for a long period of time after implantation. These considerations are based on extrapolation of observations on quantitative analyses of implants of $^{125}I$ labelled BMP impregnated PMMA.

The yield of new bone from implants of the BMP-PMMA delivery composition compared with control implants of freely dispersed BMP (i.e., without PMMA) are shown in Tables I and II. In the absence of PMMA, BMP was free to disperse in a muscle pouch, and quantities of BMP in the range of 0.5 mg. to 1.0 mg. of BMP were rapidly absorbed and did not induce formation of grossly visible bone deposits. Two mg. doses of BMP produced barely visible deposits of bone. Five mg. doses almost invariably induced formation of deposits large enough to fill the mouse's entire thigh. The yield was only very slightly higher using 10 mg. of BMP, with the volume of new bone reaching about 44 mm³, the limits of the capacity of the limb and ipsilateral pelvis to contain bone.

The bBMP-PMMA mixture induced bone formation from quantities of bBMP previously considered too small to produce grossly visible deposits. 0.1 mg. of BMP in 16 mg. of PMMA (as previously defined) induced 1 mm³ of new bone in about 21 days. Larger quantities of BMP, 0.2 mg., produced 8 times more bone than 2.0 mg. of bBMP unenclosed in PMMA. Implants of 0.5 mg. to 1.0 mg. produced 50% to about 75% as much bone as 5 mg. to 10 mg. of free bBMP.

It will be understood that it is intended to cover all changes and modifications of the example of the invention herein chosen for the purpose of illustration which do not constitute departures from the spirit and scope of the invention.

I claim:

1. A composition comprising substantially pure bone morphogenetic protein and a polymeric acrylic ester.

2. A delivery composition for delivering bone morphogenetic protein to induce formation of new bone in viable tissue comprising substantially pure bone morphogenetic protein and polymethylmethacrylate.

3. The delivery composition for delivering bone morphogenetic protein to induce formation of new bone in viable tissue, comprising bone morphogenetic protein and polymethylmethacrylate wherein the weight ratio of bone morphogenetic protein to polymethylmethacrylate is at least 0.05 parts bone morphogenetic protein to 16 parts polymethylmethacrylate.

4. The delivery composition of claim 3 wherein said weight ratio is in the range of up to 2.0 parts bone morphogenetic protein to 16 parts polymethylmethacrylate.

5. The delivery composition of claim 3 including in said composition a radioopacifying agent.

6. The delivery composition of claim 3 including in said composition an antibiotic.

7. The method of preparing a delivery composition for deliverying bone morphogenetic protein to induce formation of new bone in viable tissue comprising the step of admixing bone morphogenetic protein and polymethylmethacrylate in a weight ratio of at least 0.05 parts bone morphogenetic protein to 16 parts polymethylmethacrylate.

8. The method of claim 7 including the step of admixing liquid methylmethacrylate monomer with the bone morphogenetic protein polymethylmethacrylate admixture.

9. The method of claim 8 wherein the ratio of polymethylmethacrylate to methylmethacrylate is about 2 to 1, weight in grams to volume in milliliters.

10. The method of inducing formation of new bone in viable tissue comprising implanting in viable tissue a delivery composition comprising bone morphogenetic protein and polymethylmethacrylate wherein the weight ratio is at least 0.05 parts bone morphogenetic protein to 16 parts polymethylmethacrylate.

* * * * *